United States Patent
Brandeis

(10) Patent No.: US 10,265,266 B2
(45) Date of Patent: Apr. 23, 2019

(54) FOAM FORMATION DEVICE AND METHOD

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

(*) Notice: Subject to any disclaimer, the term of this patent is extended or adjusted under 35 U.S.C. 154(b) by 178 days.

(21) Appl. No.: 15/028,965

(22) PCT Filed: Oct. 1, 2014

(86) PCT No.: PCT/IL2014/050862
§ 371 (c)(1),
(2) Date: Apr. 13, 2016

(87) PCT Pub. No.: WO2015/052702
PCT Pub. Date: Apr. 16, 2015

(65) Prior Publication Data
US 2016/0250143 A1     Sep. 1, 2016

Related U.S. Application Data

(60) Provisional application No. 61/890,272, filed on Oct. 13, 2013.

(51) Int. Cl.
*A61K 9/00* (2006.01)
*B01F 5/06* (2006.01)
(Continued)

(52) U.S. Cl.
CPC ............ *A61K 9/0019* (2013.01); *A61K 9/122* (2013.01); *A61M 3/005* (2013.01); *A61M 5/19* (2013.01);
(Continued)

(58) Field of Classification Search
CPC ..... A61K 9/0019; A61K 9/122; A61M 3/005; A61M 5/19; B01F 3/04446; B01F 5/0605;
(Continued)

(56) References Cited

U.S. PATENT DOCUMENTS 5,492,535 A    2/1996  Reed et al.
5,868,708 A    2/1999  Hart et al.
(Continued)

FOREIGN PATENT DOCUMENTS

DE    3328530    2/1985
GB    526145     9/1940
(Continued)

OTHER PUBLICATIONS

Invitation Pursuant to Rule 137(4) EPC and Article 94(3) EPC dated Jun. 16, 2017 From the European Patent Office Re. Application No. 14803252.7. (1 Page).
(Continued)

*Primary Examiner* — Queenie S Dehghan

(57) ABSTRACT

A handheld device for mixing a liquid and a gas to form foam before a treatment procedure comprises: an inlet for letting a liquid enter the device, the inlet adapted for attachment to a syringe containing the liquid, an outlet for letting a formed foam exit the device, a chamber containing a gas, the chamber comprising the inlet and outlet, at least one agitation element disposed in the chamber, the at least one agitation element is arranged for independent movement in at least one degree of freedom, the at least one agitation element sized and shaped to mechanically agitate liquid flowing past the at least one agitation element, the liquid flowing in an overall inlet-to-outlet direction, the agitation being sufficient for the at least some of the liquid to mix with the gas to produce the formed foam; the device is dimensioned for holding in one hand.

19 Claims, 12 Drawing Sheets

(51) Int. Cl.
*A61M 5/19* (2006.01)
*B01F 13/00* (2006.01)
*A61K 9/12* (2006.01)
*B01F 3/04* (2006.01)
*B01F 7/00* (2006.01)
*A61M 3/00* (2006.01)

(52) U.S. Cl.
CPC ........ *B01F 3/04446* (2013.01); *B01F 5/0605* (2013.01); *B01F 5/0667* (2013.01); *B01F 5/0681* (2013.01); *B01F 5/0685* (2013.01); *B01F 5/0696* (2013.01); *B01F 5/0697* (2013.01); *B01F 7/00908* (2013.01); *B01F 7/00916* (2013.01); *B01F 13/0023* (2013.01); *B01F 13/0052* (2013.01); *B01F 2215/0034* (2013.01)

(58) Field of Classification Search
CPC .... B01F 5/0667; B01F 5/0681; B01F 5/0685; B01F 5/0696; B01F 5/0697; B01F 7/00908; B01F 7/009; B01F 7/00916; B01F 13/0023; B01F 13/0052
See application file for complete search history.

(56) References Cited

U.S. PATENT DOCUMENTS

| | | | |
|---|---|---|---|
| 6,962,576 | B2 | 11/2005 | Sibbitt |
| 8,177,740 | B1 * | 5/2012 | McGlothlin .......... A61M 5/152 604/82 |
| 2001/0009989 | A1 | 7/2001 | Sibbitt |
| 2002/0010418 | A1 | 1/2002 | Lary et al. |
| 2002/0010487 | A1 | 1/2002 | Evans et al. |
| 2003/0069549 | A1 | 4/2003 | MacMahon et al. |
| 2003/0097114 | A1 | 5/2003 | Ouriel et al. |
| 2004/0004521 | A1 | 1/2004 | Hasegawa |
| 2006/0184130 | A1 | 8/2006 | Sibbitt, Jr. et al. |
| 2007/0244429 | A1 * | 10/2007 | Nguyen .......... A61B 17/00008 604/89 |
| 2010/0042117 | A1 | 2/2010 | Kim et al. |
| 2011/0152683 | A1 | 6/2011 | Gerrans et al. |
| 2012/0090620 | A1 | 4/2012 | Deutsch |
| 2013/0261538 | A1 | 10/2013 | Miyazaki et al. |
| 2016/0242790 | A1 | 8/2016 | Brandeis |
| 2016/0263319 | A1 | 9/2016 | Brandeis |

FOREIGN PATENT DOCUMENTS

| | | |
|---|---|---|
| WO | WO 2004/112569 | 12/2004 |
| WO | WO 2007/114934 | 10/2007 |
| WO | WO 2009/104189 | 8/2009 |
| WO | WO 2009/109967 | 9/2009 |
| WO | WO 2009/120432 | 10/2009 |
| WO | WO 2015/052702 | 4/2015 |
| WO | WO 2015/052703 | 4/2015 |
| WO | WO 2015/052704 | 4/2015 |

OTHER PUBLICATIONS

Communication Pursuant to Article 94(3) EPC dated Jan. 31, 2018 From the European Patent Office Re. Application NO. 14803252.7. (4 Pages).
Communication Relating to the Results of the Partial International Search dated Feb. 4, 2015 From the International Searching Authority Re. Application No. PCT/IL2014/050863.
International Preliminary Report on Patentability dated Apr. 28, 2016 From the International Bureau of WIPO Re. Application No. PCT/IL2014/050862.
International Preliminary Report on Patentability dated Apr. 28, 2016 From the International Bureau of WIPO Re. Application No. PCT/IL2014/050863.
International Preliminary Report on Patentability dated Apr. 28, 2016 From the International Bureau of WIPO Re. Application No. PCT/IL2014/050864.
International Search Report and the Written Opinion dated Feb. 10, 2015 From the International Searching Authority Re. Application No. PCT/IL2014/050862.
International Search Report and the Written Opinion dated Feb. 23, 2015 From the International Searching Authority Re. Application No. PCT/IL2014/050863.
International Search Report and the Written Opinion dated Feb. 23, 2015 From the International Searching Authority Re. Application No. PCT/IL2014/050864.
Eckmann "Polidocanol for Endavenous Microfoam Sclerosant Therapy", Expert Opinion on Investigational Drugs, 18(2): 1919-1927, Dec. 2009.
Official Action dated May 25, 2018 From the US Patent and Trademark Office Re. U.S. Appl. No. 15/028,969. (18 pages).

* cited by examiner

FOAM FORMATION DEVICE AND METHOD

RELATED APPLICATIONS

The present application is a National Phase of PCT Patent Application No. PCT/IL2014/050862 having International filing date of Oct. 1, 2014, which claims the benefit of priority under 35 USC § 119(e) of U.S. Provisional Patent Application No. 61/890,272 filed on Oct. 13, 2013. The contents of the above applications are all incorporated by reference as if fully set forth herein in their entirety.

PCT Patent Application No. PCT/IL2014/050862 is related to co-filed, co-pending and co-assigned PCT Patent Application Nos. PCT/IL2014/050864 and PCT/IL2014/050863, both by the same inventor, Zeev Brandeis. PCT Patent Application No. PCT/IL2014/050864 relates to devices and methods for synchronized injection and aspiration. PCT Patent Application No. PCT/IL2014/050863 relates to devices and methods for vein ablation by irritation. The contents of the above applications are all incorporated by reference as if fully set forth herein in their entirety.

FIELD AND BACKGROUND OF THE PRESENT INVENTION

The present invention, in some embodiments thereof, relates to a foam formation device and, more particularly, but not exclusively, to a foam formation device for forming foam suitable for intrabody medical treatment.

Foam is a mixture of a gas (e.g., air, carbon dioxide) and a liquid. Foam has medical applications, for example, a foam sclerosant drug (i.e., made from liquid sclerosant) is used to close off unwanted blood vessels, for example, to treat varicose veins (refluxing saphenous vein), reticular varicosities, telangiectasia, and/or other vessel malformations.

In some cases, the foam form is used instead of the liquid drug. For example, in a blood vessel, foam is diluted less in the blood, and foam provides better contact with the surface wall. Also, the presence of gas in the foam allows for ultrasound imaging of the foam in the blood vessel. Overall, foam is believed to be safer than the liquid counterpart.

EckMann D M, "Polidocanol for endovenous microfoam sclerosant therapy", Expert Opin Investig Drugs. 2009 December; 18(12):1919-27. discloses "foamed sclerosants are typically produced by cyclical mechanical agitation of the liquid agent in the presence of a gas to generate the froth used for intravascular injection. Commonly this is simply achieved by hand using room air as the gas and rapid, manual displacement of the mixture between two syringes joined by a stopcock or between a syringe and a drug vial to manufacture the foam." In order to use the manual practices described, the operator is required to manually assemble the set-up to produce the foam. Producing the foam is time consuming, and may also require extensive physical effort. The production of the foam is performed in an unregulated manner, producing foam with unknown, or uncertain properties.

SUMMARY OF THE PRESENT INVENTION

An aspect of some embodiments of the present invention relates to a device for mixing a liquid comprising a therapeutically active substance and a biocompatible gas to form a foam, the foam being formed by agitation by one or more agitation elements.

According to an aspect of some embodiments of the present invention there is provided a handheld device for mixing a liquid and a gas to form foam before a treatment procedure, the device comprising: an inlet for letting a liquid enter the device, the inlet adapted for attachment to a syringe containing the liquid; an outlet for letting a formed foam exit the device; a chamber containing a gas, the chamber comprising the inlet and the outlet; and at least one agitation element disposed in the chamber, the at least one agitation elements are arranged for independent movement in at least one degree of freedom, the at least one agitation element sized and shaped to mechanically agitate liquid flowing past the at least one agitation element, the liquid flowing in an overall inlet-to-outlet direction, the agitation being sufficient for the at least some of the liquid to mix with the gas to produce the formed foam; wherein the device is dimensioned so as to be held in one hand.

According to some embodiments of the invention, the liquid is a liquid sclerosant and the foam is a foam sclerosant suitable for injection into a blood vessel.

According to some embodiments of the invention, about 50%-90% of the liquid passing through the chamber is formed into the foam in a single inlet-to-outlet pass through the chamber.

According to some embodiments of the invention, the at least one agitation element are not mechanically connected to one or both of each another and walls of the chamber.

According to some embodiments of the invention, the at least one agitation element is spherical so that the liquid is agitated by the flow around the at least one agitation element.

According to some embodiments of the invention, the chamber is sealed and contains carbon dioxide gas.

According to some embodiments of the invention, the at least one agitation elements are sequentially arranged along a longitudinal axis of the chamber so that the liquid flows in near proximity to each of the agitation elements.

According to some embodiments of the invention, the chamber is sized and shaped to confine the agitation elements to motion along a longitudinal axis of the chamber so that liquid is agitated by the motion.

According to some embodiments of the invention, the at least one agitation elements are sized and shaped for being retained within said chamber.

According to some embodiments of the invention, the outlet is sized and shaped to mechanically attach to a hollow lumen suitable for intrabody drug delivery, so that the produced foam is directly injected into the patient.

According to some embodiments of the invention, the at least one agitation elements are one or both of different sizes and different shapes.

According to some embodiments of the invention, the at least one agitation element is sized and shaped so as to be displaceable in all directions within the chamber so that the liquid is agitated by the displacement motion of the at least one agitation element.

According to some embodiments of the invention, the at least one agitation elements are sized and shaped so as to be rotatable so that the liquid is agitated by the rotation.

According to some embodiments of the invention, the at least one agitation elements are arranged for displacement in a radial direction so that the liquid is agitated by the radial motion.

According to some embodiments of the invention, the at least one agitation element is resilient, so that the liquid is agitated by compressive and tensile motions of the resilient elements caused by the flow of the liquid through the chamber.

According to some embodiments of the invention, the at least one resilient elements are springs arranged with windings around a longitudinal axis of the chamber, parallel to the inlet-to-outlet direction, so that the compressive and tensile motions occur in the inlet-to-outlet direction. Optionally, the resilient element comprises at least one resistive feature having a collective surface area sufficiently large to utilize the force of the fluid flow through the chamber to compress the resilient elements.

According to some embodiments of the invention, the at least one agitation elements comprises at least one agitation feature on an external surface thereof so that the liquid encounters the at least one agitation features to set the agitation elements in motion, the liquid being agitated by the at least one agitation features or the motion.

According to some embodiments of the invention, the at least one agitation element extends at least along 50% of a path from the inlet-to-outlet direction.

According to some embodiments of the invention, the chamber is divided into a plurality of subchambers with different types of the at least one agitation element in each of the subchambers.

According to an aspect of some embodiments of the present invention there is provided a kit for forming a foam for medical treatment by injection, the kit comprising: the foam formation device as described herein, and a syringe suitable for injection of the foam into a patient.

According to an aspect of some embodiments of the present invention there is provided a device for medical treatment comprising: an elongated hollow tube having a proximal end for accepting a liquid from outside the body of a patient and a distal end for insertion into a blood vessel, the elongated hollow tube being sized for insertion into the blood vessel; a plurality of blades arranged to agitated the liquid in the elongated hollow tube so that the liquid is mixed with a gas to form a foam, as the liquid flows in a proximal to distal direction through the blades, so that the formed foam is directly injected into the blood vessel through the distal end.

According to some embodiments of the invention at least a distal portion of the elongated hollow tube is a rigid needle.

According to some embodiments of the invention the blades are arranged so that about 50%-90% of the liquid is formed into the foam.

According to an aspect of some embodiments of the present invention there is provided a method of hand producing foam for medical treatment from a liquid before a medical procedure, the method comprising: applying a mechanical pressure by using a finger, to a syringe comprising a medically active liquid, to displace the liquid in an overall proximal-to-distal direction along an axis, so that the liquid is sufficiently agitated during displacement by encountering at least one agitation element, the at least one agitation elements arranged for independent movement in at least one degree of freedom, so that at least some of the liquid is mixed with a gas to form a medically active foam suitable for injection into a patient.

According to some embodiments of the invention, the foam is a sclerosing foam.

According to some embodiments of the invention, about 50%-90% of the liquid is formed into foam during a single pass of the proximal-to-distal displacement.

According to some embodiments of the invention, the method further comprises selecting a suitable foam formation device to produce the medically foam having at least one preselected foam parameters.

According to some embodiments of the invention, the selecting comprises selecting according to software that uses mathematical models to estimate the at least one preselected foam parameters produced by the suitable foam formation device.

According to some embodiments of the invention, the method further comprises proximally connecting a first container containing the liquid, distally connecting a second container, displacing the liquid from the first container through the foam formation device in the proximal-to-distal direction to form the foam, and collecting the formed foam in the second container. Optionally, the method further comprises displacing the foam and remaining liquid from the second container into the foam formation device, in a distal-to-proximal direction, forming additional foam, and collecting the additional formed foam in the first container.

According to some embodiments of the invention, the method further comprises injection the foam into the patient.

According to some embodiments of the invention, the foam is injected into a blood vessel of a patient to close off the blood vessel.

According to an aspect of some embodiments of the present invention there is provided a handheld device for mixing a liquid and a gas to form foam before a treatment procedure, the device comprising: an inlet for letting a liquid enter the device, the inlet adapted for attachment to a syringe containing the liquid; an outlet for letting a formed foam exit the device; a chamber containing a gas, the chamber comprising the inlet and the outlet; and at least one wire convolutedly arranged wire disposed in the chamber, the at least one wire sized and shaped to mechanically agitate liquid flowing between strands of the at least one wire, the liquid flowing in an overall inlet-to-outlet direction, the agitation being sufficient for the at least some of the liquid to mix with the gas to produce the formed foam; wherein the device is dimensioned so as to be held in one hand.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the present invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the drawings.

DESCRIPTION OF SPECIFIC EMBODIMENTS OF THE INVENTION

Figure 1:
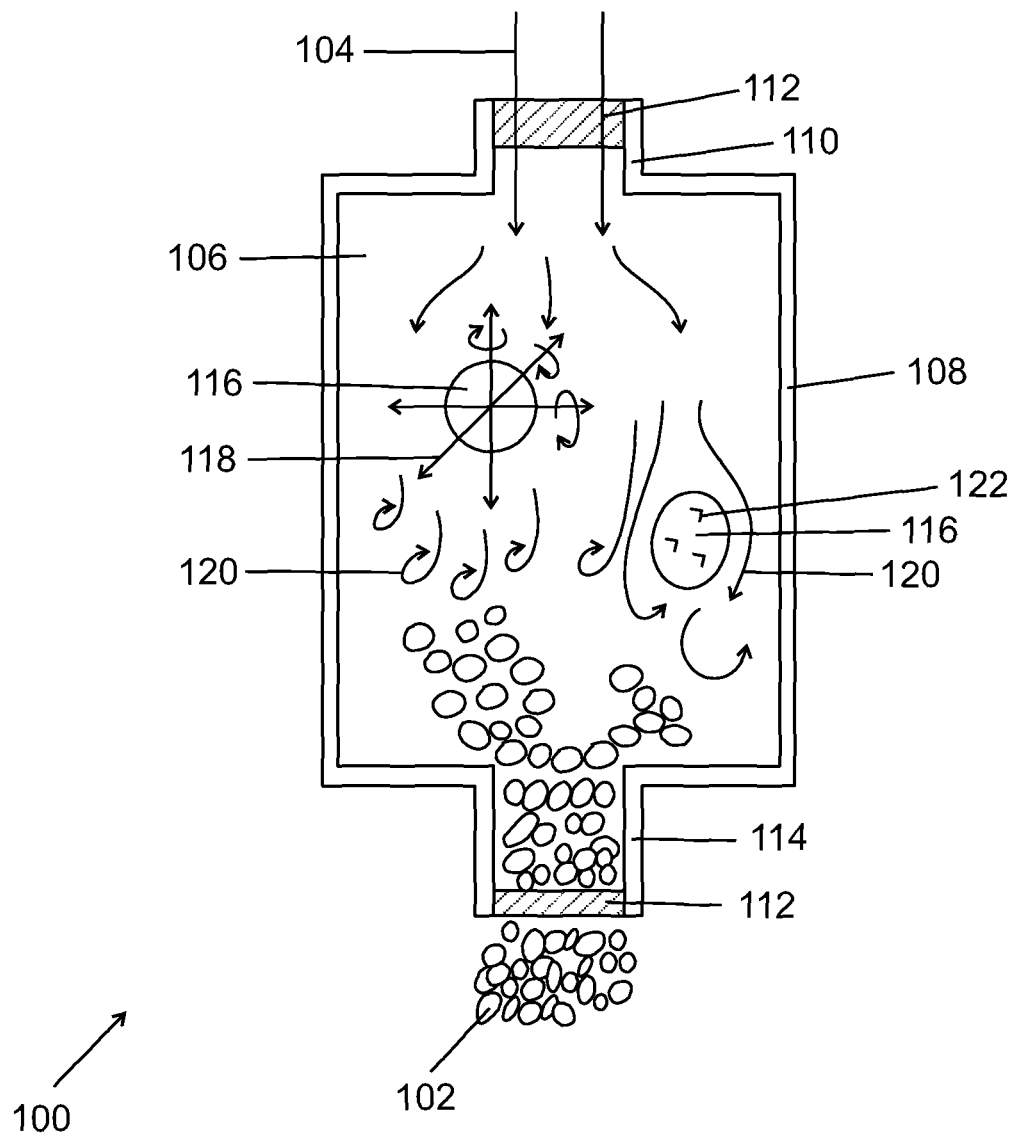
FIG. 1 is a schematic illustration of the foam formation device, in accordance with exemplary embodiments of the present invention.

An aspect of some embodiments of the present inventions relates to a device for mixing a liquid and a gas to form a foam, the mixing occurring by displacement of the liquid in an overall direction from an inlet to an outlet, so that the flowing liquid encounters one or more agitation elements that agitate the liquid so that foam is formed. Optionally, the amount of foam formed is clinically selected, for example, to induce the closing off of a blood vessel. Advantageously, the foam may be formed by an operator within a relatively short period of time, with relatively little physical efforts, and/or without requiring special training and/or single handedly.

As used herein the term "overall" means an average or net movement of the fluid in a direction, even if on a smaller scale some of the fluid is moving in an opposite direction during the agitation and/or foam formation.

In exemplary embodiments, the device produces an amount of foam that is adapted clinically for a medical treatment session by a single pass of the liquid through the device, for example selected according to a respective medical procedure. Alternatively, two, three, four or more passes of the liquid through the device are required. The liquid may be passed from the inlet to the outlet, or from the outlet to the inlet. Alternatively or additionally, the total dose of liquid is split into multiple smaller liquid doses, and each liquid dose is passed once through the device to form foam. Advantageously, the number of passes may be less than would be required using other methods, which may provide for a faster way to make foam with less physical effort.

Optionally, the device is not designed to produce foam as part of a commercial manufacturing process, for example, mass production. Optionally, the device is designed to produce the amount of foam required for the selected medical procedure, and not, for example, quantities for multiple procedures. Optionally, the device is designed for production of foam right before bestowing the foam for injection.

Optionally, the device is dimensioned and/or designed to be handheld. Optionally, the device is dimensioned and/or designed to be used by one hand. Alternatively or additionally, two hands are required.

Optionally, the device is adapted for detachable connection and/or use with commonly available container, for example, disposable standard syringes.

In exemplary embodiments, each inlet-to-outlet pass through the device converts about 50%-90% of the liquid into the foam, or for example, about 20%-70%, or about 30%-80%, or about 60%-99%, or about 80%-100% of the liquid is converted to foam, or other smaller, intermediate or larger percentage ranges are available. Alternatively or additionally, each inlet-to-outlet pass through the device forms about 0.5 cc-50 cc of foam, or about 1 cc-5 cc, or about 5-30 cc, or about 5 cc-10 cc, or other smaller, intermediate or larger volume ranges.

In exemplary embodiments, the device comprises of a chamber containing a gas and one or several agitation elements. The agitation elements agitate the liquid as the liquid flows from the inlet to the outlet.

Optionally, the agitation of the liquid occurs as the liquid encounters the agitation element, causing the liquid to suddenly change directions and/or turbulent flow. Alternatively or additionally, the agitation elements are displaced within the flowing liquid, the agitation of the liquid occurring by the displacement of the elements through the flowing liquid. The displacement of the agitation elements may occur by mechanical pressure exerted by the flowing liquid, for example, the agitation elements are resilient elements (e.g., springs) that are compressed by the flowing liquid, and that agitate the liquid upon re-expansion.

Optionally, the agitation elements are not mechanically connected to one another. Alternatively, some or all of the agitation elements are mechanically connected to one another.

Optionally, the agitation elements are not mechanically connected to the chamber, for example the chamber wall. Alternatively, some or all of the agitation elements are mechanically connected to the chamber.

In exemplary embodiments, the agitation elements occupy most of a path along the inlet-to-outlet direction, for example, along the longitudinal axis. For example, the agitation elements occupy at least 50% of the path, or at least 60%, or at least 70%, or at least 80%, or at least 90%, or at least 95%, or other smaller, intermediate or larger percentages.

In exemplary embodiments, the device is detachably connectable to a syringe (or other suitable container) containing the liquid. Manually pressing a plunger (e.g., using a finger) of the syringe forces the liquid out of the syringe, and through the device to form the foam. Optionally, the pressure is applied in a gentle manner, for example, without requiring excessive exertion such as finger pain and/or other muscle strain. The foam may be collected at the outlet by a suitably connected device, for example, another syringe or a collection container. Alternatively, the foam is directly injected, if a needle, catheter or other lumen is attached to the outlet. Advantageously, the foam may be produced in a manner that is suitable for direct injection. Advantageously, the foam may be produced while reducing the risk of external contamination.

Optionally, the device is selected to produce foam according to one or more preselected foam parameters. Advantageously, the device may be used to form foam with predictable properties, for example, within a range or distribution curve.

In exemplary embodiments, the foam is a foam sclerosant suitable for injection into a blood vessel of a patient. Optionally, the foam is suitable for closing off unwanted veins, for example, to treat varicose veins.

In exemplary embodiments, the device is sterile. Advantageously, the device may reduce the risk of contamination of the foam.

An aspect of some embodiments of the present invention relates to a method for mixing a liquid and a gas to form a foam suitable for treatment by injection into the body of a patient, the method comprising displacing a liquid drug along an axis, so that the liquid is agitated during the displacement by encountering one or more agitation elements, thereby mixing the liquid with the gas to form a clinically significant amount of a medically active foam suitable for injection into a patient.

Optionally, one or more foam properties are selected for the foam produced for the treatment session. Optionally, the foam is produced to have the one or more preselected foam properties.

The present invention, in some embodiments thereof, relates to a foam formation device and, more particularly, but not exclusively, to a foam formation device for forming foam suitable for intrabody medical treatment.

Before explaining at least one embodiment of the present invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic of a foam formation device 100, in accordance with exemplary embodiments of the present invention. Device 100 forms foam 102 from a liquid 104, by agitating liquid 104 so that liquid 104 mixes with a gas 106 to form foam 102. Advantageously, the foam may be formed from the liquid by the application of a gentle pressure, without requiring additional agitation and/or displacement of the liquid, and/or without requiring a complex setup.

In exemplary embodiments, device 100 comprises a chamber 108. Optionally, chamber 108 is preloaded with gas 106, for example with carbon dioxide or other suitable gases. Alternatively, chamber 108 is filled with room air. Advantageously, chamber 108 allows for formation of foam containing s pre-selected gas.

Chamber 108 contains an inlet 110 for allowing liquid 104 to enter device 100. Optionally, chamber 108 contains an outlet 114 for allowing foam 102 (and/or remaining liquid 104) to exit device 100. Alternatively, there is a single inlet 110 into chamber 108, inlet 110 also acting as an outlet for removing of the foam. Alternatively, there are multiple inlets 110 into chamber 108, the multiple inlets 110 allowing multiple fluids to be inserted into chamber 108, for example, to form a foam of a mixture of the multiple fluids. Alternatively or additionally, there are multiple outlets, for example, one outlet for removal of foam and one outlet for removal of liquid, the foam removal outlet located above the liquid removal outlet as foam will float over the liquid.

Optionally, inlet 110 and/or outlet 114 are sealed by suitable plugs 112. Optionally, plugs 112 hermetically and/or pressure seal chamber 108. Chamber 118 may be provided with gas 106 under pressure, or the pressure therein may be about atmospheric pressure. Plugs 112 may also provide a seal against needles inserted into chamber 108 through plugs 112. Alternatively or additionally, plugs 112 are removable.

Optionally, the internal contents of chamber 108 are provided sterilized.

In exemplary embodiments, and as will be described in more detail herein, chamber 108 contains one or more agitation elements 116 sized and shaped to mechanically agitate liquid 104. Optionally, liquid 104 is agitated as liquid 104 flows in an overall inlet 110 to outlet 114 direction. The agitation exerted is enough to mix at least some of liquid 104 with gas 106 to form foam 102.

Optionally, the energy to agitated liquid 104 to form foam 102 is at least provided by moving liquid 104, for example, by a user pushing a plunger on a syringe to force liquid 104 from the syringe into chamber 108.

Optionally, liquid 104 is agitated by changes in flow and/or turbulent flow induced by agitation elements 116. The turbulent flow is provided by the presence of the agitation elements 116. Liquid 104 flowing over the surface of elements 116 may be forced to repeatedly change directions, potentially causing turbulent flow and/or mixing of liquid 104 with gas 106 to form foam 102. The turbulent motion and subsequent foam formation indicated by curving arrows 120.

Optionally, at least some agitation elements 116 are fixed in place, for example, packed in chamber 108 and/or connected to the internal wall of chamber 108. Alternatively or additionally, at least some agitation elements are free to move within chamber 108, for example, being spaced apart. Optionally, at least some agitation elements (e.g., all of the elements) have independent movement in at least one or more of six degrees of freedom (shown as arrows 118), able to move in one or more directions: up, down, left, right, forward, reverse, pitch, roll, and/or yaw. Alternatively, at least some elements are fixed so that motion is restricted in certain directions only, for example, only along the radial axis of chamber 108 and/or only along the longitudinal axis of chamber 108.

Optionally, agitation elements 116 are small discrete shapes, for example, spheres, ellipsoids, boxes, and/or other shapes. Alternatively or additionally, agitation elements 116 are long and/or interconnected, for example, twisted and/or convoluted wires.

Optionally, all agitation elements 116 in chamber 108 are of the same type. Alternatively, there are different types of agitation elements 116 in chamber 108, for example, different sizes and/or different shapes.

Optionally, agitation elements 116 contain agitation features 122. Optionally, agitation features 122 are sized, shaped and/or positioned to increase the formation of foam 102, for example, by causing additional turbulent flow to liquid 104.

Some examples of possible shapes and related advantages include:

Spheres—may allow for higher overall flow in the inlet-to-outlet direction during foam formation, as the liquid flows over the surface. Spheres may be more easily adjustable to obtain the desired foam parameters, for example, changing the size of the spheres, changing the number of spheres.

Squares—may allow for more turbulence of the liquid and more foam production relative to the spheres, as the liquid is suddenly blocked by the surface of the square.

Wires—may allow for wider distribution in foam parameters (e.g., bubble size), as the spaces between the wires may be randomly positioned.

Alternatively or additionally, agitation features 122 are sized, shaped and/or positioned to increase motion of the agitation elements 116, for example, elements 116 are distally displaced and/or rotated.

Some examples of possible agitation features and related advantages include:

Grooves on the surface or tunnels through the agitation element—May direct the fluid flowing through the groove or tunnel to collide with fluid flowing in other areas to form foam at the intersection.

Small spheres attached to the surface of the agitation element—May increase the turbulence of the fluid flowing over the surface of the agitation element to form foam.

Spikes or vertical pads on the surface of the agitation element—May increase the turbulence of the fluid more than the spheres. May resist the flowing fluid so that the agitation element rotates along an axis.

Optionally, surface features 122 are sized, shaped and/or positioned to provide foam 102 according to one or more preselected parameters.

The size (e.g., diameter) of elements 116 are, for example, about 1-5 millimeters (mm), or about 0.1-1 mm, or about 0.01-0.1 mm, or about 1-10 micrometers, or other smaller, intermediate or larger sizes are used. Optionally, the element sizes are selected according to the produced foam properties.

The elements 116 are made from suitable materials that are biocompatible and/or do not react with the drug, for example, stainless steel.

Advantageously, one or more foam parameters may be selectable and/or controllable by the movement of the agitation elements, for example, allowing for greater possible movements of the agitation elements may allow for a higher percentage of liquid to be converted into foam. For example, restricting the motion of the agitation elements may allow for more precise control over the foam, for example, the bubble size within the foam may be within a smaller range.

Advantageously, foam formation device 100 may be manufactured using low cost methods for example, injection molding.

Advantageously, foam formation device 100 may be disposable.

Figure 2:
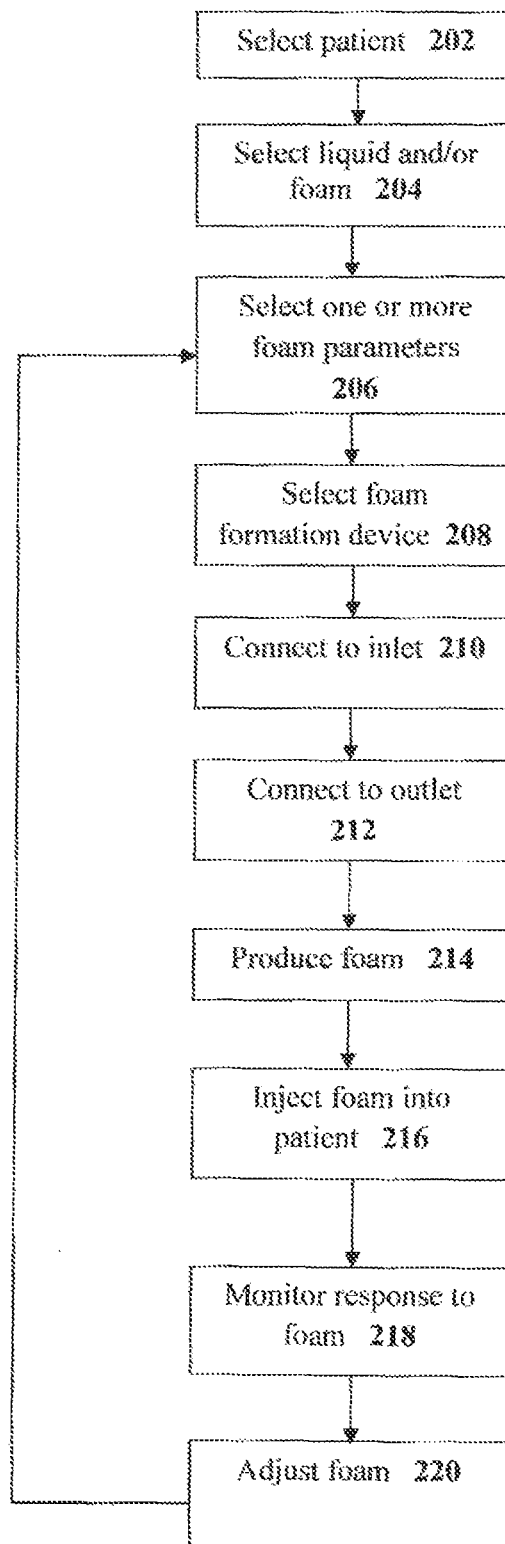
FIG. 2 is a flowchart of a method of using a foam formation device, for example a foam formation device as depicted in FIG. 1, in accordance with exemplary embodiments of the present invention.

Reference is now also made to FIG. 2, which is flowchart of a method of forming foam from a liquid and a gas, in accordance with exemplary embodiments of the present invention, for example using the foam formation device as described with reference to FIG. 1. Optionally, the method forms foam with one or more preselected parameters. Optionally, the foam is suitable for medical treatment of a patient. Optionally, only the amount of foam required for the medical procedure is produced, potentially, only small amount of foam or no foam may be wasted. Advantageously, the method may be performed without requiring additional external materials and/or complex set-ups, for example, tubing, several syringes, valves, or other intermediate structures. Advantageously, the foam formation method and/or device may allow for the formation of foam having one or more predetermined parameters. Advantageously, the foam formation method and/or device may allow for the predictable and/or repeatable formation of foam according to the one or more predetermined parameters. Advantageously, the foam formation method may form foam having very small bubbles, for example, on the order of micrometers. Small bubbles may advantageous, as the resulting foam may be stable for longer (before breakdown back into liquid), and/or may have a larger surfaces area of active drug to contact the walls of the anatomical treatment area.

Optionally, the foam is formed within a relatively short period of time, for example, in no more than about 10 seconds, or about 30 seconds, or about 60 seconds, or other smaller, intermediate or larger time periods. Advantageously, the relatively quick formation of foam saves time for the physician and/or patient.

Optionally, the foam formation is performed only with displacement of the liquid in the inlet-to-outlet direction and/or a proximal-to-distal direction. Optionally, no back and forth motion of the liquid is required and/or no additional external agitation (e.g., shaking the device) is required for the foam formation.

Figure 4A:
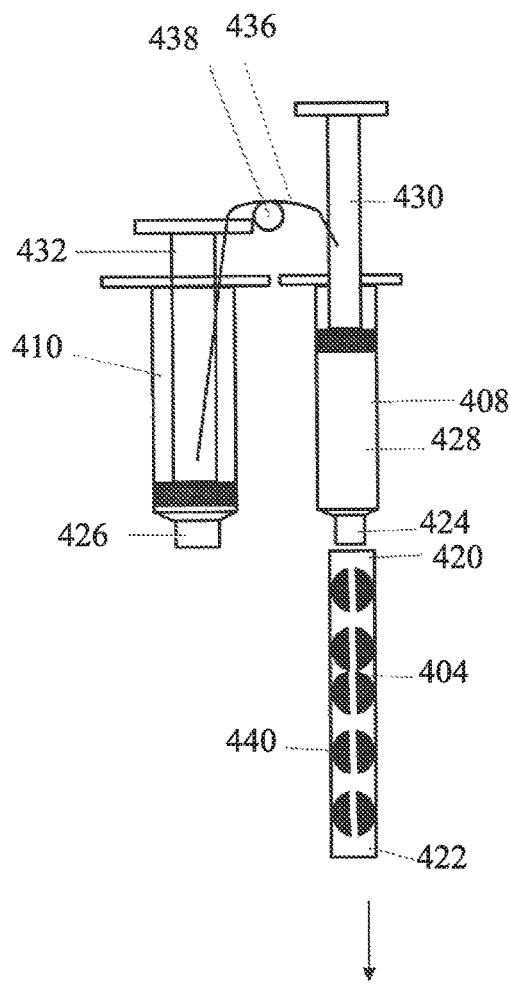
FIGS. 4A-4B are simplified schematics illustrating use and/or adjustment of the foam formation device, in accordance with exemplary embodiments of the present invention.
Figure 4B:
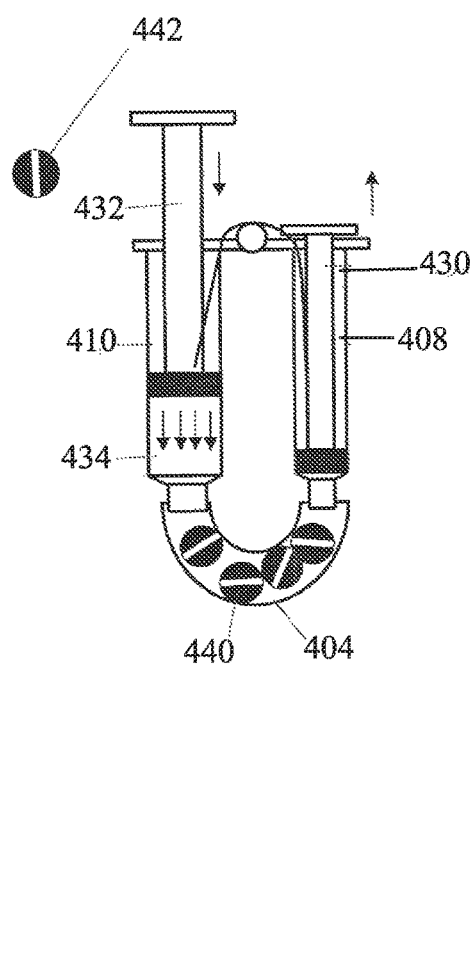

Optionally, the foam formation is performed by the application of manual pressure. Optionally, the manual pressure is applied by one finger, for example, the thumb, for instance using a device as depicted in FIGS. 4A-B. Optionally, the manual pressure is applied gently, for example, by the user pushing with the finger without experiencing strain or pain of the finger, for instance using a device as depicted in FIGS. 4A-B. Advantageously, the method may be performed without painfully straining the muscles of the user.

Optionally, at 202, a patient is selected for medical treatment using the foam produced by the foam formation device, in accordance with embodiments of the present invention.

Optionally, the patient is selected for treatment of varicose veins. Optionally, the patient is selected to undergo closure of the veins, for example, the greater saphenous vein, the small saphenous vein, a recurrence of a previous treatment, collateral vessels, or other veins. Alternatively, the patient is selected for treatment of other vessel malformations for example, a spider vein, a varicose vein, hemorrhoids, and/or varicocele. Alternatively, the patient is selected for application of foam into a body cavity.

Optionally, at 204, a suitable liquid medicine is selected for the formation of the foam, in accordance with embodiments of the present invention. Optionally, the liquid medicine is diluted in a liquid carrier, for example, normal saline. Optionally, the liquid is a sclerosant, for example, sodium tetradecylsulphate (e.g., about 0.1-3%), and/or polidocanol (e.g., about 0.5-3%).

Optionally, the liquid is pre-sterilized. Alternatively, the liquid is unsterilized. The foam formed from the unsterilized liquid may be sterilized, or the unsterilized foam may be used in locations where sterility is not critical.

At 206, one or more foam parameters are selected, in accordance with exemplary embodiments of the present invention. Not necessarily limiting examples of the foam parameters include:

The range of foam bubble sizes: Optionally, a certain percentage of the foam bubbles fall within a preselected size range. Advantageously, the foam selection method and/or device may allow for relatively small bubbles as compared to other methods and/or devices, for example, microbubbles. Without being bound to theory, a relatively smaller bubble size allows for a relatively higher sclerosant concentration in the foam, less risk of dilution of the foam in blood and/or a larger surface area for increased contact between sclerosant and vessel wall endothelium. Optionally, relatively small agitation elements and/or agitation features are selected to produce foam having the preselected foam bubble sizes.

The volume of liquid per treatment session: for example, the volume of sclerosant per treatment session. For example, about 1 milliliter (mL), about 5 mL, about 10 mL, about 30 mL, about 50 mL, or other smaller, intermediate or larger volumes. The volume may be selected, for example, based on the size of the treatment area, the safety profile of the drug and/or the medical state of the patient.

The ratio of liquid to gas: for example, about 0.3:1, about 0.5:1, about 1:1, about 1:3, about 1:6, about 1:10, or other smaller, intermediate or larger values. Optionally, the volume of gas within the chamber and/or the volume of sclerosant for the treatment are selected according to the ratio of liquid to gas. More gas may improve ultrasound imaging of the foam. Less gas may form smaller bubbles.

The type of gas: for example, carbon dioxide, oxygen, room air. Advantageously, relatively safer gases may be selected. For example, carbon dioxide may have a reduced risk of forming emboli as compared to room air.

Optionally, the one or more foam parameters may be determined according to clinical experiments and/or a numerical simulation of the medical substance in various body cavities and/or venous lumens. Optionally, the one or more foam parameters are determined according to the target vein in which the administration is performed. As different veins have different characteristics, such as width and/or an estimated blood flow, the one or more foam parameters may be changed. For example, the one or more foam parameters may be set differently at the great saphenous vein or at the small saphenous vein.

At 208, the foam formation device is selected, in accordance with exemplary embodiments of the present invention.

Optionally, the foam formation device is selected to produce foam having the one or more foam parameters (as in box 206). The selection may be performed according to a calibrated table of foam parameters and foam formation devices (e.g., manual selection by a user). Alternatively or additionally, the selection may be performed according to software that uses mathematical models to estimate the foam parameters produced by a corresponding foam formation device. The calibration table and/or software may be produced based on experiments of forming foam using foam formation devices with known properties, measuring the parameters of the resulting foam, and calibrating the device with the produced foam.

Alternatively or additionally, the foam selection device is selected according to other factors, for example, physician preference, to comply with the volume of liquid used, to comply with the size of the treatment area, or other factors. Some examples of selectable variables of the foam formation device include:

Volume of the chamber and/or diameter of the chamber: Larger sizes may allow for faster foam formation rates. Smaller sizes may result in more complete foam formation and/or a larger percentage of liquid being converted into foam. Chamber volumes are, for example, about 0.1 milliliter (mL), about 0.5 mL, about 1 mL, about 3 mL, about 5 mL, about 10 mL, about 30 mL, about 50 mL, or other smaller, intermediate or larger volumes. Chamber diameters are, for example, about 0.5 mm, about 1 mm, about 3 mm, about 5 mm, about 10 mm, about 15 mm, or other smaller, intermediate or larger diameters. Optionally, the chamber is sized to fit within a needle or lumen for direct insertion into the body.

Size, shape and/or number of agitation elements, spaces between agitation elements: Larger elements, more agitation elements and/or larger spaces may form foam faster with a higher percentage of liquid converted. Fewer elements, smaller elements and/or smaller spaces may form foam with smaller bubble sizes.

At 210, the inlet of the foam formation device is directly or indirectly connected (e.g., through a tube) to a container with the liquid medicine to be formed into foam, in accordance with embodiments of the present invention. For example, a preloaded syringe is attached to the inlet.

At 212, the outlet of the foam formation device is directly or indirectly connected to a container suitable for storing the formed foam, in accordance with embodiments of the present invention. For example, a second empty syringe or other container are connected to the outlet. Alternatively, the outlet is connected to a tube suitable for direct injection of the foam into the patient, for example, a needle or a catheter.

At 214, the foam is produced, in accordance with embodiments of the present invention. As described in more detail herein below, but briefly summarized, in exemplary embodiments, liquid is distally displaced through the inlet into the container. The liquid is agitated by the one or more agitation elements so that the liquid mixes with the gas forming the foam. The foam is removed from the outlet.

Optionally, the produced foam has one or more of the preselected foam parameters as in box 206.

At 216, the produced foam is injected into the anatomical site of the patient for medical therapy, for example, into a vein.

Optionally, a dose of foam is produced and then injected. For example, an amount of foam is produced and collected in a needle. The needle is used to inject the patient. More foam may be produced and injected as required. Alternatively, the dose is created on the fly and injected as the foam is created, for example, by using a catheter with the foam formation device on or near the distal end thereof.

Optionally at 218, the response to the foam by the patient is monitored.

Optionally, monitoring is performed within a short period of time after and/or during the procedure. For example, the patient is clinically observed and/or examined for venous spasm. In another example, the vein is imaged using ultrasonography for the presence of a thin white line on the venous wall. Alternatively or additionally, long term monitoring is performed. For example, the patient is examined weeks or months after the treatment to look for recurrence.

Optionally, at 220, one or more foam parameters are adjusted, in accordance with embodiments of the present invention. Foam parameters may be adjusted to obtain the selected clinical effect, for example, the bubble distribution size may be increased or decreased. The foam parameters may be adjusted, for example, by replacing the foam formation device, and/or by adding, removing and/or replacing the agitation elements within the foam device.

Optionally, the adjustment is performed in response to the monitoring as in 218. Optionally, the adjustment is performed if the desired effect is not obtained.

Optionally, the adjustment is performed during the procedure. Alternatively or additionally, the adjustment is performed as part of another different procedure.

Optionally, the adjustment comprises of selecting a different foam parameter (as in 206), for example, a different bubble size distribution.

Optionally, the adjustment comprises of using a new foam formation device. Optionally, the used foam formation device may be single use and disposable. Alternatively, the existing foam formation device is changed, for example, by changing one or more of the agitation elements in the container.

FIGS. 3A-3D are block diagrams showing some possible fluid communication connections to the inlet and/or outlets of a form formation device 304, in accordance with exemplary embodiments of the present invention. Advantageously, the foam formation device may be connected to different containers, which may provide flexibility in operation to the user.

Figure 3A:
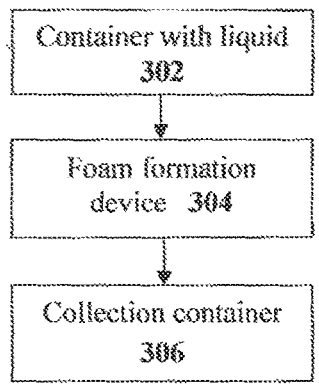
FIGS. 3A-3D are block diagrams illustrating exemplary connections to the foam formation device, in accordance with exemplary embodiments of the present invention.

FIG. 3A is a block diagram illustrating a container with treatment liquid 302 connected to foam formation device 304 through the inlet. A collection container (e.g., vial) 306 is connected to the outlet. Optionally, collection container 306 is empty. Liquid flows from container 302 (e.g., syringe), to device 304 (shown by arrow). Foam formed by device 304 flows out to container 306 (shown by arrow). Pressure to flow the liquid and/or form may be provided by any suitable methods, for example, manually by a user, automatically by a pump, by pressurized gas, at least partially by gravity, or other suitable methods.

Advantageously, the setup of FIG. 3A may be useful for quickly forming foam, by reducing the number of passes of liquid through the foam formation device, for example, a single pass. Advantageously, foam may be formed in seconds. The foam may be mostly maintained in a sterilized state, as formation of the foam does not require building a complex setup, or excessive transfer between containers, thereby limiting or preventing contamination by exposure from the external environment.

Optionally, the setup forms foam single handedly. For example, the physician may hold the foam formation device in the palm of the hand using the fingers, and press the plunger of the syringe to form foam with the thumb. Advantageously, the physician may only use one hand to form foam, leaving a free hand to perform other tasks.

Connections between containers and the foam formation device may be achieved by different suitable methods, for example, through threads, friction, without significant contact, glue, premolding, or other suitable methods. Connections may be direct, or indirect through another fluid communication device, for example, a hollow tube.

Figure 3B:
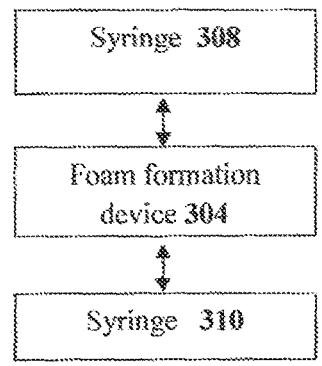

FIG. 3B is a block diagram illustrating two syringes 308 and 310 attached to the inlet and outlet of device 304. Optionally, standard syringes may be used, for example, 5 mL, 10 mL, 20 mL, or other syringe sizes that are generally commonly available in clinics, operating rooms and/or on hospital wards. Advantageously, the syringes may be disposable, may be in sterile packaging, may be commonly available in clinics, may be low cost, and/or may be designed to form fluid tight seals with the treatment device.

Optionally, syringes 308 and 310 are used to flow liquid and/or foam through device 304, in a forward direction or in a reverse direction. In one mode of operation, syringe 308 is preloaded with the liquid and syringe 310 is empty. Pressing a plunger of syringe 308 displaces the liquid through device 304 to fill syringe 310 with foam. Remaining unfoamed liquid in device 304 and/or syringe 310 may be pushed back through device 304 so that newly formed foam is now collected in syringe 308. Alternatively or additionally, the created foam in syringe 310 is passed back again through device 304 to syringe 308.

Advantageously, the setup of FIG. 3B may be used to make sure that all or most of the liquid has been foamed by passing unfoamed liquid again through the device. Advantageously, the setup may be used to break up large foam bubbles into smaller foam bubbles, to help make foam with a more uniform bubble size, by passing the formed foam again through the device.

Figure 3C:
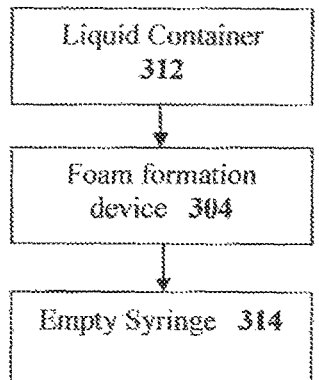

FIG. 3C is a block diagram of a container with liquid 312 connected to the inlet of device 304. An empty syringe (or other container) 314 is connected to the outlet. Liquid flows (shown by arrow) from container 312 to device 304. Foam flows (shown by arrows) from device 304 to syringe 314. Optionally, flow of liquid and/or foam is achieved by applying a suction force to the outlet of device 304, for example, by pulling the plunger of empty syringe 314.

Advantageously, the setup of FIG. 3C may be sold as a preassembled kit that may be quickly used to form foam. In one example, the container is preloaded with the drug and preassembled to the inlet of device 304. To use, the physician inserts a needle into the device outlet and pulls the syringe. The suction force pulls the liquid through the device, forms the foam and pulls the foam into the syringe. Advantageously, no or minimal assembly is required, and/or there is no requirement to transfer the liquid and/or foam from one container to another in order to form and/or inject.

Figure 3D:
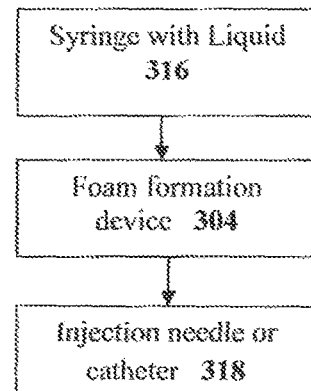

FIG. 3D is a block diagram of form formation device 304 arranged so that upon formation of the foam, the foam is directly injected into a patient. A syringe (or other container) containing the drug 316 is attached to the inlet of device 304. An injection needle or catheter is attached to the outlet of device 304. Alternatively, the device 304 and the needle or catheter are formed into a single element, for example, the needle contains agitation elements therein. Foam formed in device 304 that exits from the outlet enters the needle or catheter, and is directly deposited in the body of the patient.

Advantageously, foam may be formed as needed and on the fly.

FIGS. 4A-4B are schematic illustrations corresponding to the block diagram of FIG. 3B, in accordance with exemplary embodiments of the present invention.

FIG. 4A shows the separate components and FIG. 4B shows the assembled components. An inlet 420 of device 404 is attached to an opening 424 of a syringe 408 containing a liquid drug 428. An outlet 422 of device 402 is attached to an opening 426 of an optionally empty syringe 410. Optionally, the attachment is achieved by friction and/or threads between the inner walls of the inlet and/or outlet and the outer walls of the opening of the syringes. Alternatively, the syringes contain needles that pierce plugs on inlets of the device.

Pressing on a plunger 430 of syringe 408 forces drug 428 through device 404 and into syringe 410. As shown in FIG. 4B, optionally, formed foam 434 (and optionally unformed liquid 428) collected in syringe 410 is directed back through device 404, in the outlet-to-inlet direction (as shown by arrows) to be collected by syringe 408. The force to displace formed foam 434 and/or remaining liquid provided by a plunger 432 of syringe 410.

Optionally, plungers 432 and 430 are connected by a mechanism so that forward displacement of one plunger prevents simultaneous forward displacement of another plunger. Optionally, the mechanism is arranged so that forward displacement of one plunger causes reverse displacement of the corresponding plunger. Optionally, the mechanism comprises of a wire 436 having one end attached to one plunger and another end attached to another plunger, wire 436 passing through a pulley 438. Advantageously, the mechanism prevents or reduces pressure buildup within the system, and/or helps ensure that liquid travels from one syringe to the other.

FIGS. 4A-4B also illustrate an example of the adjustment of device 404, for example as described with reference to box 220 of FIG. 2. In the example shown, device 404 shown in FIG. 4A comprises five agitation elements 440. One element 442 has been removed from device 404. Device 404 in FIG. 4B now comprises four elements 440.

Figure 5:
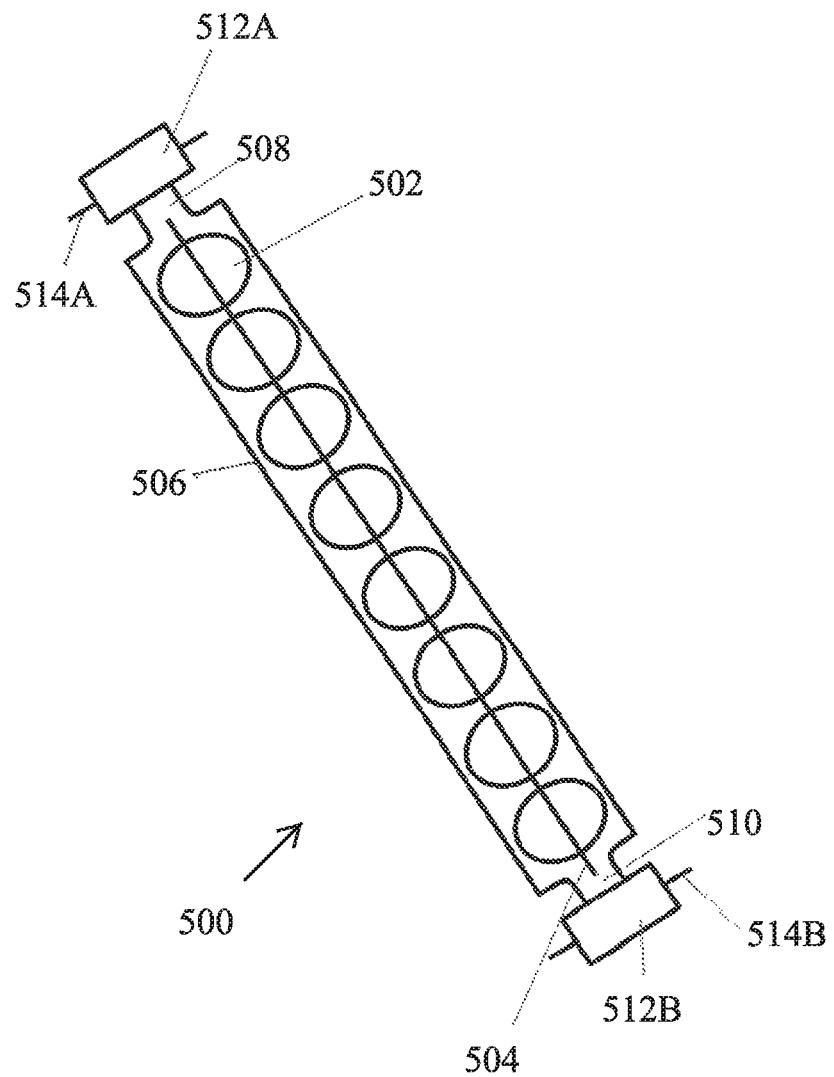
FIG. 5 is a schematic illustration of a linear arrangement of the agitation elements of the foam formation device, in accordance with embodiments of the present invention.

FIG. 5 is a schematic illustration of a sequential arrangement of one or more agitation elements 502 of a foam formation device 500, in accordance with embodiments of the present invention. Optionally, elements 502 are spheres.

Optionally, agitation of the liquid occurs by flow over the surface of elements 502. Alternatively or additionally, agitation of the liquid occurs by rotation and/or displacement of elements 502 along the longitudinal axis.

Optionally, elements 502 are sequentially arranged along a longitudinal axis of device 500.

Optionally, at least some elements 502 are spaced apart. Alternatively, at least some elements 502 are touching one another.

Optionally, a retaining structure, for example, a wire 504, is attached to the elements 502, so that the elements retain their relative positions. Alternatively or additionally, no retaining structure is used, so that elements 502 are able to be displaced along the longitudinal axis and/or rotated.

Alternatively or additional, a chamber 506 of device 500 is sized and/or arranged so that elements 502 are at least partially confined in their respective positions. Optionally, the diameter of chamber is less than the diameter of two elements 502, so that elements 502 are retained within their respective positions along the longitudinal axis. Alternatively or additionally, an inlet 508 and/or outlet 510 have a neck and/or restriction with an internal diameter less than that of elements 502, so that elements 502 are retained within chamber 506.

Optionally, caps 512A and/or 512B seal inlet 508 and/or outlet 510. Optionally, caps 512A-B comprise a corresponding flange 514A-B. Flanges 514A-B may help manual removal of caps 512A-B.

Optionally, liquid flowing from inlet 508 to outlet 510 flows in near proximity to every element 502 within chamber 506. Optionally, every element 502 agitates the liquid. Advantageously, the formation of foam according to one or more parameters (e.g., bubble size distribution) may be predicted with improved accuracy.

Figure 6:
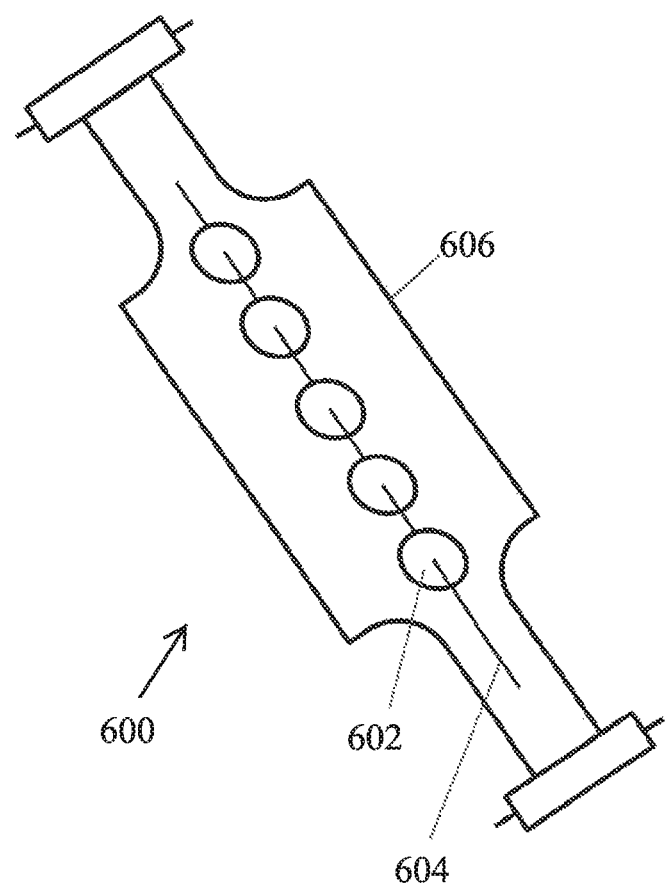
FIG. 6 is a schematic illustration of an arrangement of radially displaceable agitation elements, in accordance with embodiments of the present invention.

FIG. 6 is a schematic illustration of a foam formation device 600 with an arrangement of radially displaceable agitation elements 602, in accordance with embodiments of the present invention. In the interest of brevity, the description of device 600 will be focused on differences relative to device 500 as shown in FIG. 5.

Optionally, in addition to and/or instead of the agitation described in FIG. 5, the agitation of liquid is applied by the radial motion of elements 602.

Optionally, elements 602 are sequentially arranged along a resilient wire 604. Optionally, wire 604 is radially displaceable, allowing for radial displacement of elements 602. For example, wire 604 is made out of a resilient material, such as a tightly wound spring. Optionally, wire 604 is arranged to allow for simultaneous displacement of elements 602 in different radial directions, for example, if wire 604 forms a sine wave during vibration.

Optionally, container 606 has an internal diameter that is large enough to accommodate the radial displacement of elements 602.

Optionally, the energy for radial displacement of elements 602 is provided by the flowing liquid. For example, the initial volume of liquid applies pressure to some elements 602 in a first radial direction. The tension build-up in wire 604 is then released. Vibrating wire 604 or the recoil of wire 604 agitates the liquid in chamber 606.

Figure 7:
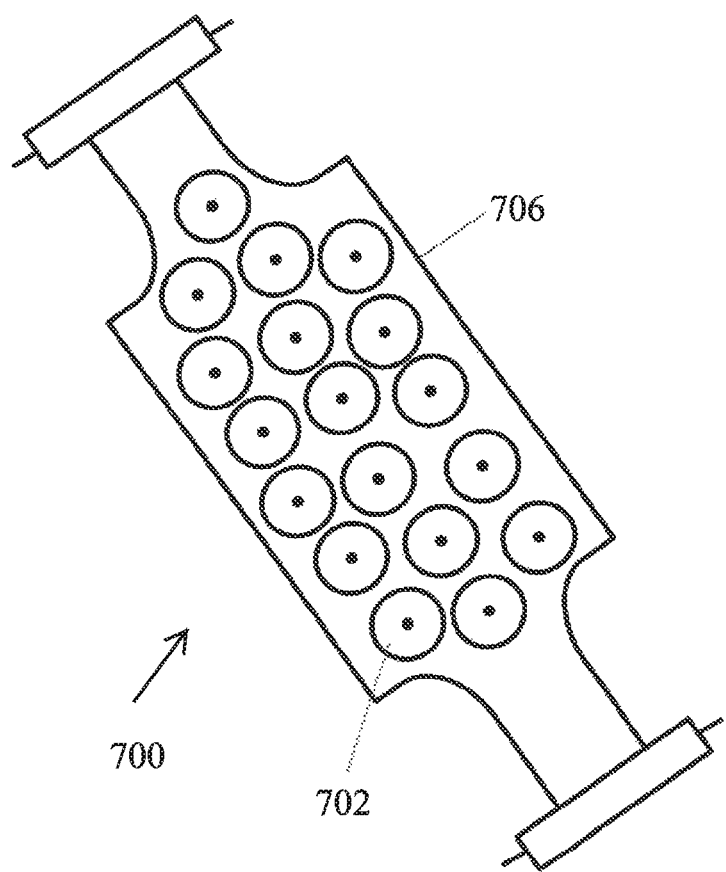
FIG. 7 is a schematic illustration of an arrangement of agitation elements that may rotate and/or move omnidirectionally, in accordance with embodiments of the present invention.

FIG. 7 is a schematic illustration of a foam formation device 700 with an arrangement of omnidirectional motion and/or rotational motion of agitation elements 702, in accordance with embodiments of the present invention. Alternatively, agitation elements are packed together so that even rotational motion is reduced or prevented. In the interest of brevity, the description of device 700 will be focused on differences relative to device 500 as shown in FIG. 5.

Optionally, the number, size and/or shape of elements 702 are selected so that elements 702 are omnidisplaceable within chamber 706, in six degrees of freedom. Optionally, agitation by elements 702 of the liquid is performed omnidirectionally.

Alternatively, the number, size and/or shape of elements 702 are selected so that elements 702 are confined to be rotationally displaceable (pitch, roll, yaw) but not displaceable, for example, elements 702 are packed within chamber 706. Optionally, agitation by elements 702 of the liquid is performed by the rotating elements 702.

Optionally, the diameter of chamber 706 is larger than the diameter of two elements 702.

Optionally, the length of chamber 706 is longer than the length of two elements 702.

Advantageously, chamber 706 allows more fluid flow as compared to chamber 506, so that foam may be produced at a faster rate.

FIGS. 8A-8D are schematic illustrations of exemplary agitation features of the agitation elements, in accordance with embodiments of the present invention. Optionally, agitation of the liquid occurs by the liquid flowing over the agitation features. Alternatively or additionally, the liquid flowing over the agitation features causes the agitation elements to rotate. The rotation of the agitation elements may cause additional agitation of the liquid.

Advantageously, the agitation features may increase the agitation of the liquid and may result in faster foam formation and/or more accurate foam formation according to one or more foam formation parameters.

Figure 8A:
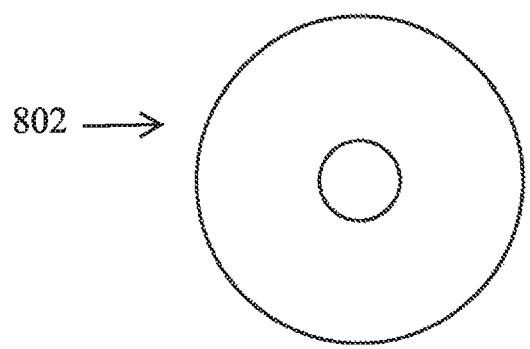
FIGS. 8A-8D are schematic illustrations of exemplary agitation features of the agitation elements, in accordance with embodiments of the present invention.

FIG. 8A is a schematic of a spherical agitation element 802 without agitation features. Optionally, agitation occurs by liquid flowing over the surface of element 802.

Figure 8B:
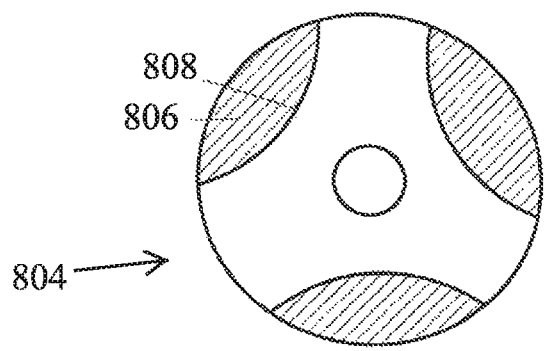

FIG. 8B is a schematic of a spherical agitation element 804, with one or more portions removed 806. Removed portions 806 result in element 804 with various surface contours, forming one or more agitation features 808.

Figure 8C:
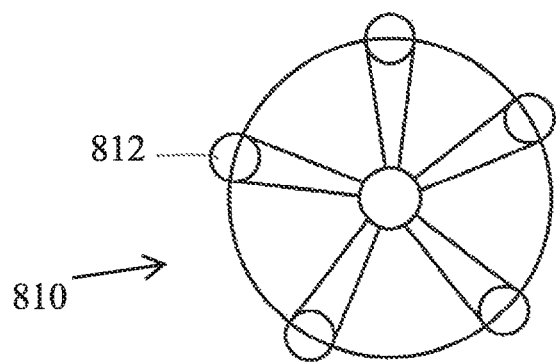

FIG. 8C is a schematic of a spherical agitation element 810, having one or more conduit 812 agitation features therethrough. Optionally, conduits 812 connect with one another inside element 810, providing fluid communication between different areas around element 810. Optionally, agitation occurs within element 810 by the liquid flowing through conduits 812 and/or by the liquid emerging from conduits 812 at different locations on the surface of element 810.

Figure 8D:
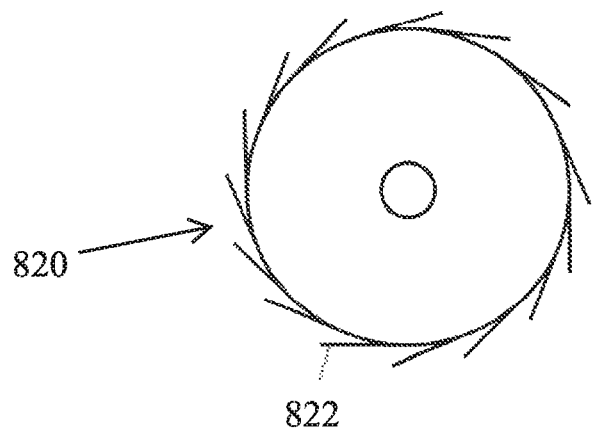

FIG. 8D is a schematic of a spherical agitation element 820 having a number of extension 822 agitation features. Extensions 822 are arranged in a turbine pattern so that liquid flowing in an overall direction encounters at least some of extensions 822, causing element 820 to spin.

Figure 9:
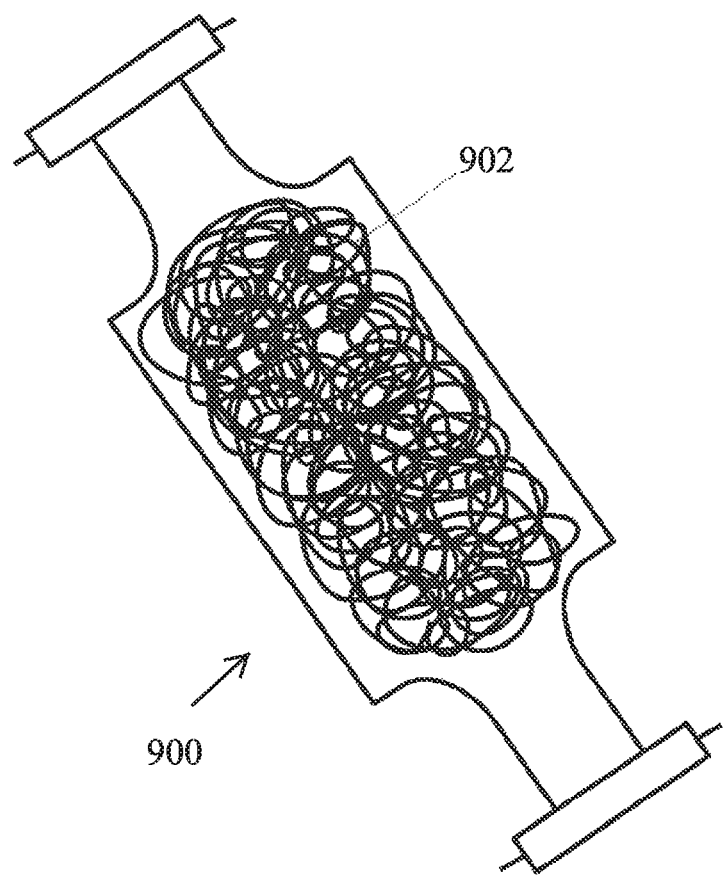
FIG. 9 is a schematic illustration of one or more wires as agitation elements, in accordance with embodiments of the present invention.

FIG. 9 is a schematic illustration of one or more convoluted wires 902 as agitation elements, in accordance with embodiments of the present invention. Optionally, wires 902 have a thin diameter, for example, the diameter of wires 902 is similar to the diameter of a spherical agitation element as described herein. Optionally, wires 902 are convoluted so that there is spacing between adjacent loops of wires 902.

Optionally, the liquid is forced to travel in the spaces between the tightly convoluted wires 902. Optionally, the agitation is caused by the liquid moving through the wires.

Advantageously, spaces between wires 902 may be set to be larger than spaces between spherical agitation elements, as small agitation elements tend to pack tightly together in the container.

Figures 10A, 10B:
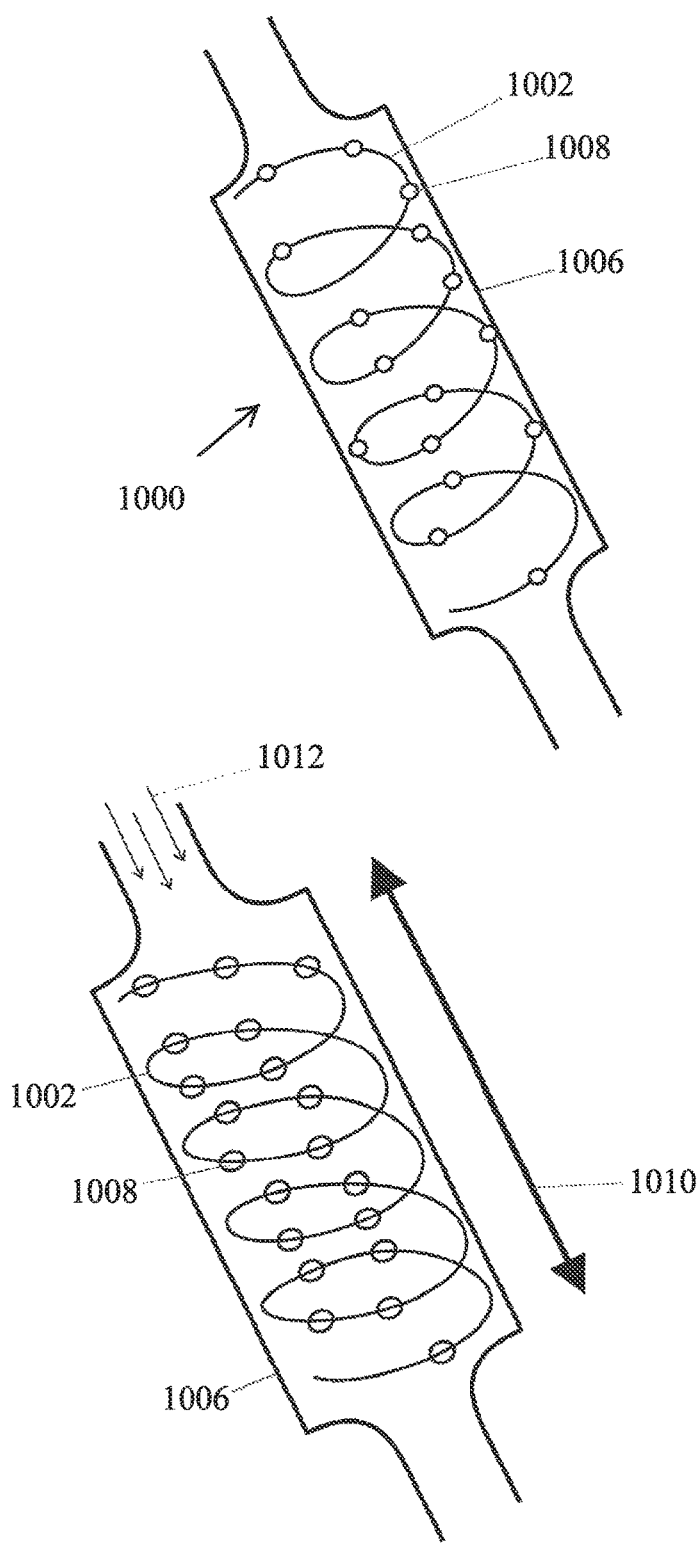
FIGS. 10A-10B are schematics illustrations of a resilient agitation element, in accordance with embodiments of the present invention.

FIGS. 10A-10B are schematic illustrations of a foam formation device 1000 with one or more resilient agitation elements 1002, in accordance with embodiments of the present invention. Not necessarily limiting examples of the resilient elements include a spring, a bellows, a nitinol wire, and/or an elastic rod. Advantageously, the resilient element may provide additional agitation by converting some of the energy in the moving liquid into agitation.

FIG. 10A illustrates the spring agitation element 1002 in a container 1006 without liquid flow. Optionally, spring 1002 is arranged for compression and extension displacement motion along a longitudinal axis of container 1006. Optionally, spring 1002 is arranged with windings around the longitudinal axis, and/or the longitudinal axis of spring 1002 is coaxial with the longitudinal axis of container 1006. Optionally, spring 1002 is arranged with windings arranged parallel to and/or coaxial with the inlet-to-outlet direction.

Optionally, spring 1002 is made of a thin wire. Optionally, the diameter of the wire and/or spacing between adjacent wire loops and/or other springs are selected to agitate the liquid to produce foam according to one or more predetermined parameters.

Optionally, spring 1002 comprises one or more resistive features 1008, for example, flat plates, spheres (e.g., as described with reference to FIGS. 8A-8D), rod-like extensions, boxes, wire loops, or other shapes. Optionally, resistive features 1008 are spaced apart along spring 1002. Optionally, some resistive features 1008 are in a fixed position along spring 1002. Alternatively or additionally, some resistive features 1008 are arranged along spring 1002 to allow displacement motion along spring 1002 and/or rotational motion.

FIG. 10B is a schematic illustration showing spring 1002 of FIG. 10A re-expanding (arrows 1010) against liquid 1012. Re-expansion may occur after liquid compressing spring 1002 has been reduced in force by slowing down. In one example, inserting liquid 1012 into chamber 1006 in pulses may cause spring to repeatedly compress and re-expand.

Optionally, the resistive features have a collective surface area sufficiently large to utilize the force of the fluid flow through the chamber to at least partially compress spring 1002.

Optionally, liquid 1012 is agitated by the re-expansion of spring 1002. Optionally, liquid 1012 is agitated by resistive features 1008.

Figure 11B:
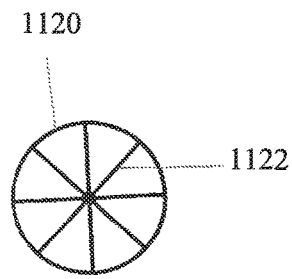
FIGS. 11B-C are front views of some exemplary turbine agitation elements.
Figure 11C:
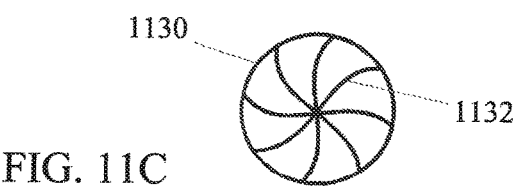
Figure 11A:
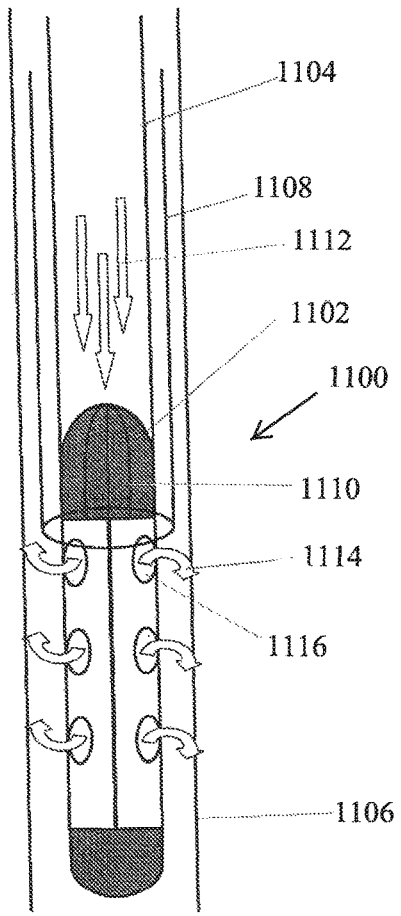
FIG. 11A is a schematic illustration of a turbine agitation element at the end of a lumen inserted into a vein of a patient, in accordance with exemplary embodiments of the present invention.

FIG. 11A is a schematic illustration of a foam formation device 1100 comprising a turbine agitation element 1102 at the end of a lumen 1104 inserted into a vein 1106 of a patient, in accordance with exemplary embodiments of the present invention. Optionally, liquid 1112 is agitated into foam 1114 by agitation element 1102. Optionally, foam 1114 enters the treatment site in vein 1106 through one or more openings 1116 of lumen 1104. Optionally, openings 1116 face the vessel wall so that released foam 1114 is directed towards the vessel wall.

Optionally, the agitation occurs in near proximity to the treatment site. Optionally, the agitation occurs are required, only forming the foam as needed at the time of treatment.

Optionally, lumen 1104 is a rigid needle suitable for injection through tissue. Alternatively, lumen 1104 is a flexible catheter, optionally sized for insertion through an external catheter sheath 1108.

Optionally, agitation element 1102 includes a turbine, for example a turbine having a plurality of blades 1110. In use, blades 1110 agitate liquid flow 1112 by disruption of the flow of the liquid. Alternatively, any of the agitation devices and/or agitation elements described hereinabove may be used with the catheter.

FIG. 11B is a front view of a turbine agitation element 1120, in accordance with embodiments of the present invention. Optionally, turbine blades 1122 are arranged in a radial pattern.

FIG. 11C is a front view of a turbine agitation element 1130, in accordance with embodiments of the present invention. Optionally, turbine blades 1132 are arranged in a radial curving pattern. Optionally, the curving pattern further agitates the liquid flowing through by causing the liquid to flow in a spiral.

Optionally, some blades of the turbine agitation elements are arranged in parallel to the longitudinal axis of the insertion lumen. Alternatively or additionally, some blades of the turbine are angled relative to the longitudinal axis of the insertion lumen. The angulations of the blades may further agitate the liquid by causing the liquid to flow in a spiral.

Figure 12:
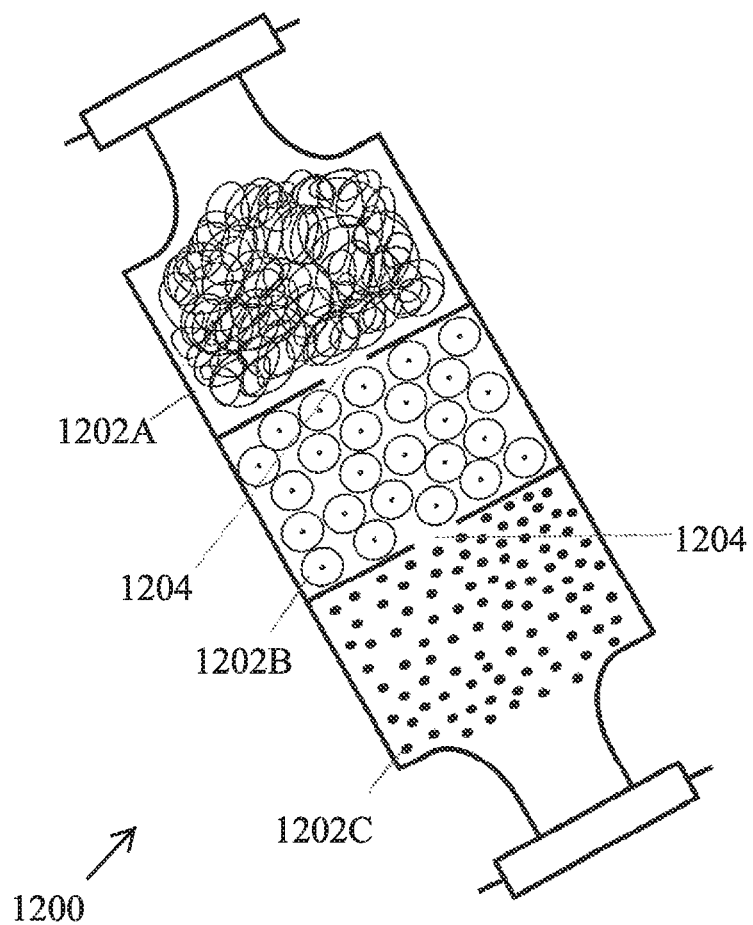
FIG. 12 is a schematic illustration of a foam formation device with two or more different types of agitation elements, in accordance with exemplary embodiments of the present invention.

FIG. 12 is a schematic illustration of a foam formation device 1200 with two or more different types of agitation elements, in accordance with exemplary embodiments of the present invention. Advantageously, the device with the different types of agitation elements may produce foam with the preselected foam parameters.

Optionally, device 1200 is divided into two or more chambers. Optionally, each chamber houses different types of agitation elements. For example, as shown chamber 1202A houses the wire agitation element as described with reference to FIG. 9, chamber 1202B houses spherical agitation elements that are packed together so that all motion is reduced or prevented, and chamber 1202C houses spherical agitation elements that are free to move in an omnidirectional manner. Optionally, the chambers may be arranged in sequential order (as shown). Alternatively or additionally, the different types of agitation elements are mixed together.

Optionally, one or more openings 1204 provide fluid communication between the chambers. Optionally, openings 1204 are smaller than the diameter of the chambers. Optionally, openings 1204 are sized so that fluid is retained in the chamber until exit through the openings 1204. Advantageously, as some fluid may take a longer path until the fluid is able to exit through openings 1204, the fluid may be further agitated.

Optionally, the foam formation device is sold in kit form.

Optionally, several foam formation devices are available, in which each foam formation device is designed to produce foam with different properties, for example, foam with different bubble distribution sizes, and/or different gases preloaded in the device. Optionally, the foam formation devices are labeled with the expected properties of the produced foam.

Optionally, the foam formation device is sold along with one or more syringes and/or collection containers. Optionally, one or more of the syringes are preloaded with the liquid. Alternatively or additionally, one or more of the syringes are empty. Optionally, the syringes are pre-connected to the inlet and/or outlet of the device. Optionally, the package is labeled with the type and/or dose of the preloaded liquid.

Optionally, the foam formation device is sold along with the body insertion lumen (e.g., catheter, needle). Optionally, the form formation device is pre-connected to the lumen. Optionally, the foam formation device is sold individually in different sizes, being compatible with different sized lumens.

It is expected that during the life of a patent maturing from this application many relevant foam formation devices will be developed and the scope of the term foam formation device is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the present invention, which are, for clarity, described in the context of separate embodiments, may also be provided in combination in a single embodiment. Conversely, various features of the present invention, which are, for brevity, described in the context of a single embodiment, may also be provided separately or in any suitable subcombination or as suitable in any other described embodiment of the present invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A handheld device for mixing a liquid and a gas to form foam before a treatment procedure, the device comprising:
   an inlet adapted to be attached to an opening of a first syringe containing a liquid for letting said liquid enter the device from the first syringe;
   an outlet for letting a formed foam exit from the device into a member of a group consisting of an opening of a second syringe, a needle, and a catheter;
   a chamber containing a gas, the chamber comprising the inlet and the outlet; and
   a plurality of agitation elements disposed in the chamber and connected to one another by at least one wire, the plurality of agitation elements being arranged for independent movement in at least one degree of freedom, the plurality of agitation elements sized and shaped to mechanically agitate liquid flowing past the plurality of agitation elements, the liquid flowing in an overall inlet-to-outlet direction, the agitation being sufficient for at least some of the liquid to mix with the gas to produce the formed foam;
   wherein the device is dimensioned so as to be held in one hand.

2. The device of claim 1, wherein the device is configured to mix the gas with a liquid sclerosant and to thereby form a foam sclerosant suitable for injection into a blood vessel.

3. The device of claim 1, wherein the device is configured to form about 50%-90% of the liquid passing through the chamber into the foam in a single inlet-to-outlet pass through the chamber.

4. The device of claim 1, further comprising a second plurality of agitation elements that are not mechanically connected to the plurality of agitation elements.

5. The device of claim 1, wherein the chamber is sealed and contains carbon dioxide gas.

6. The device of claim 1, wherein the plurality of agitation elements are sequentially arranged along a longitudinal axis of the chamber so that the liquid flows in near proximity to each of the plurality of agitation elements.

7. The device of claim 6, wherein the longitudinal axis is defined between the inlet and outlet of the device.

8. The device of claim 1, wherein the chamber is sized and shaped to confine the agitation elements to motion along a longitudinal axis of the chamber so that liquid is agitated by the motion.

9. The device of claim 8, wherein the longitudinal axis is defined between the inlet and outlet of the device.

10. The device of claim 1, wherein the plurality of agitation elements are sized and shaped for being retained within the chamber.

11. The device of claim 1, wherein the outlet is sized and shaped to mechanically attach to a hollow lumen suitable for intrabody drug delivery, so that the produced foam is directly injected into the patient.

12. The device of claim 1, wherein the plurality of agitation elements are one or both of different sizes and different shapes.

13. The device of claim 1, wherein the plurality of agitation elements are sized and shaped so as to be displaceable so that the liquid is agitated by the displacement motion of the plurality of agitation elements.

14. The device of claim 1, wherein the plurality of agitation elements are sized and shaped so as to be rotatable so that the liquid is agitated by the rotation.

15. The device of claim 1, wherein the plurality of agitation elements are arranged for displacement in a radial direction so that the liquid is agitated by the radial motion.

16. The device of claim 1, wherein each of the plurality of agitation elements comprises at least one agitation feature on an external surface thereof so that the liquid encounters the at least one agitation features to set the agitation elements in motion, the liquid being agitated by the at least one agitation features or the motion.

17. The device of claim 1, wherein the plurality of agitation elements extends at least along 50% of a path from the inlet-to-outlet direction.

18. The device of claim 1, wherein the device is configured to produce the formed foam within the chamber.

19. The device of claim 1, wherein the first syringe comprises a plunger, the first syringe is configured to transfer liquid into the device through depression of the plunger, and the device and first syringe are dimensioned such that a user can manually depress the plunger with a thumb of the user's hand while holding the device with the palm and fingers of said hand.

* * * * *